United States Patent
Ben-Eli et al.

(10) Patent No.: US 9,289,422 B2
(45) Date of Patent: Mar. 22, 2016

(54) INITIAL ACQUISITION USING CRYSTAL OSCILLATOR

(75) Inventors: David Ben-Eli, Modiin (IL); Alexander Zaslavsky, Petach Tikva (IL)

(73) Assignee: MARVELL WORLD TRADE LTD., St. Michael (BB)

( * ) Notice: Subject to any disclaimer, the term of this patent is extended or adjusted under 35 U.S.C. 154(b) by 624 days.

(21) Appl. No.: 13/423,221

(22) Filed: Mar. 18, 2012

(65) Prior Publication Data

US 2012/0245883 A1 Sep. 27, 2012

Related U.S. Application Data

(60) Provisional application No. 61/467,329, filed on Mar. 24, 2011.

(51) Int. Cl.
*G06F 15/00* (2006.01)
*A61K 31/4745* (2006.01)
(Continued)

(52) U.S. Cl.
CPC ............ *A61K 31/4745* (2013.01); *A61K 45/06* (2013.01); *H03L 1/026* (2013.01); *H04B 1/16* (2013.01)

(58) Field of Classification Search
CPC ......... H03L 1/026; H03L 1/025; H03L 1/027; H03L 7/00; H03L 1/00; H03L 1/028; H03L 7/08; H03L 7/1974; H03L 1/022; H03L 2207/50; H03L 7/099; H03L 7/14; G01S 19/235; H03B 5/32; H03B 21/00; H03B 5/04
USPC ............ 331/176, 66, 44, 1 A, 177 A, 34, 40; 455/255, 136, 196.1, 113, 182.1, 455/192.1, 71; 342/357.2; 702/106
See application file for complete search history.

(56) References Cited

U.S. PATENT DOCUMENTS 4,453,834 A 6/1984 Suzuki et al.
5,659,884 A 8/1997 Daughtry et al.
(Continued)

FOREIGN PATENT DOCUMENTS

CN 1379942 A 11/2002
CN 101541073 A 9/2009
(Continued)

OTHER PUBLICATIONS

Kanodia et al., MOAR: A Multi-channel Opportunistic Auto-rate Media Access Protocol for Ad Hoc Networks, 2004, Proceedings fo the First International Conference on Broadband Networks (Broadnets'04).*
U.S. Appl. No. 13/423,220 Office Action dated Sep. 18, 2013.
U.S. Appl. No. 14/242,935 Office Action dated Nov. 10, 2014.
European Patent Application # 12160331.0 Search Report dated Nov. 22, 2013.
U.S. Appl. No. 13/189,595 Office Action dated Apr. 29, 2013.
U.S. Appl. No. 12/394,056 Official Action dated Jun. 10, 2010.
U.S. Appl. No. 12/394,056 Official Action dated Dec. 1, 2010.
U.S. Appl. No. 12/394,056 Official Action dated Sep. 21, 2010.
U.S. Appl. No. 13/423,220, filed Mar. 18, 2012.

(Continued)

*Primary Examiner* — Janet Suglo
*Assistant Examiner* — Lisa Peters

(57) ABSTRACT

A method includes holding in a memory of a receiver, for each temperature in a range of temperatures, a respective first parameter indicative of a frequency error of a crystal oscillator in the receiver at the temperature, and a respective second parameter indicative of an uncertainty of the first parameter. An operating temperature of the crystal oscillator is measured. One or more frequencies, for initial acquisition of signals from a transmitter, are selected based on the first and second parameters corresponding to the measured operating temperature. The receiver is tuned to receive the signals from the transmitter on at least one of the selected frequencies.

20 Claims, 3 Drawing Sheets

(51) Int. Cl.
*H03L 1/02* (2006.01)
*H04B 1/16* (2006.01)
*A61K 45/06* (2006.01)

(56) References Cited

U.S. PATENT DOCUMENTS

| | | | |
|---|---|---|---|
| 5,757,244 A * | 5/1998 | Nonaka et al. | 331/176 |
| 5,875,388 A | 2/1999 | Daughtry, Jr. et al. | |
| 5,883,550 A * | 3/1999 | Watanabe et al. | 331/176 |
| 5,953,648 A | 9/1999 | Hutchison et al. | |
| 6,212,398 B1 | 4/2001 | Roberts et al. | |
| 6,272,190 B1 | 8/2001 | Campana | |
| 6,463,266 B1 | 10/2002 | Shohara | |
| 6,522,212 B1 | 2/2003 | Kodim | |
| 6,636,121 B2 | 10/2003 | Barak et al. | |
| 6,738,607 B2 * | 5/2004 | Ashkenazi | 455/259 |
| 6,985,705 B2 * | 1/2006 | Shohara | 455/164.1 |
| 7,221,921 B2 | 5/2007 | Maligeorgos et al. | |
| 7,307,480 B2 * | 12/2007 | Shiu et al. | 331/44 |
| 7,403,078 B2 | 7/2008 | Routama et al. | |
| 7,466,209 B2 | 12/2008 | Babitch | |
| 7,548,130 B2 | 6/2009 | Kobayashi | |
| 7,728,684 B2 | 6/2010 | Tozer | |
| 8,031,024 B1 * | 10/2011 | Zaslavsky | 331/176 |
| 2002/0158693 A1 | 10/2002 | Soong et al. | |
| 2003/0144020 A1 | 7/2003 | Challa et al. | |
| 2005/0064818 A1 | 3/2005 | Assarsson et al. | |
| 2005/0088314 A1 | 4/2005 | O'Toole et al. | |
| 2005/0093638 A1 * | 5/2005 | Lin et al. | 331/176 |
| 2006/0267703 A1 | 11/2006 | Wang et al. | |
| 2007/0165594 A1 | 7/2007 | Heinle et al. | |
| 2007/0178875 A1 | 8/2007 | Rao et al. | |
| 2007/0188254 A1 | 8/2007 | Sutardja et al. | |
| 2008/0018531 A1 * | 1/2008 | Matsumoto | 342/357.05 |
| 2009/0195322 A1 * | 8/2009 | Yan et al. | 331/44 |
| 2010/0112950 A1 | 5/2010 | Haartsen et al. | |
| 2010/0331019 A1 | 12/2010 | Bhattacharjee et al. | |
| 2011/0066297 A1 | 3/2011 | Saberi et al. | |
| 2011/0092163 A1 | 4/2011 | Baurque | |
| 2011/0176465 A1 | 7/2011 | Panta et al. | |
| 2011/0261909 A1 | 10/2011 | Andgart et al. | |
| 2011/0306315 A1 | 12/2011 | Subrahmanya et al. | |
| 2012/0069800 A1 | 3/2012 | Soliman et al. | |
| 2015/0091702 A1 | 4/2015 | Gupta et al. | |

FOREIGN PATENT DOCUMENTS

| | | |
|---|---|---|
| GB | 2368235 A | 4/2002 |
| WO | 0133870 A2 | 5/2001 |
| WO | 0247281 A1 | 6/2002 |
| WO | 2005099107 A1 | 10/2005 |

OTHER PUBLICATIONS

3GPP TS 25.211, "3rd Generation Partnership Project; Technical Specification Group Radio Access Network; Physical channels and mapping of transport channels onto physical channels (FDD) (Release 6)", V6.10.0, Chapter 5, Sep. 2009.

3GPP TS 25.214, "3rd Generation Partnership Project; Technical Specification Group Radio Access Network; Physical layer procedures (FDD) (Release 6)", V6.11.0, Annex C, Dec. 2006.

3GPP TS 25.304, "3rd Generation Partnership Project; Technical Specification Group Radio Access Network; User Equipment (UE) procedures in idle mode and procedures for cell reselection in connected mode (Release 9)", V9.3.0, Sep. 2010.

3GPP TS 36.304, "3rd Generation Partnership Project; Technical Specification Group Radio Access Network; Evolved Universal Terrestrial Radio Access (E-UTRA); User Equipment (UE) procedures in idle mode (Release 9)", V9.5.0, Dec. 2010.

3GPP TS 43.022, "3rd Generation Partnership Project; Technical Specification Group GSM/EDGE Radio Access Network; Functions related to Mobile Station (MS) in idle mode and group receive mode (Release 9)", V9.2.0, Sep. 2010.

Nihon Dempa Kogyo Co. Ltd., "NX3225SA Crystal Unit", Data Sheet, Nov. 14, 2011.

European Patent Application # 12160026.6 Extended Search Report dated Aug. 21, 2012.

CN Application # 201210085047.3 Office Action dated Sep. 29, 2015.

CN Application # 201210075636.3 Office Action dated Sep. 1, 2015.

* cited by examiner

INITIAL ACQUISITION USING CRYSTAL OSCILLATOR

CROSS-REFERENCE TO RELATED APPLICATIONS

This application claims the benefit of U.S. Provisional Patent Application 61/467,329, filed Mar. 24, 2011, whose disclosure is incorporated herein by reference.

FIELD OF THE DISCLOSURE

The present invention relates generally to communication systems, and particularly to methods and systems for performing signal acquisition in communication receivers.

BACKGROUND

Various communication protocols define acquisition processes in which a communication terminal locks on a base station signal. The Universal Mobile Telecommunications System (UMTS) specifications, for example, define such a process in "$3^{rd}$ Generation Partnership Project; Technical Specification Group Radio Access Network; Physical layer procedures (FDD) (Release 6)," TS 25.214, Annex C, December, 2006; and in "$3^{rd}$ Generation Partnership Project; Technical Specification Group Radio Access Network; Physical channels and mapping of transport channels onto physical channels (FDD) (Release 6)," TS 25.211, chapter 5, September, 2009, all of which are incorporated herein by reference.

Communication terminals use various kinds of frequency sources, such as crystal oscillators, for generating clock and Local Oscillator (LO) signals. Some types of crystal oscillators comprise internal circuitry that compensates for variations in oscillation frequency over temperature. Other types of crystal oscillators are uncompensated. Internally-compensated crystal oscillators typically provide higher frequency accuracy than uncompensated crystal oscillators, but at a higher cost.

The description above is presented as a general overview of related art in this field and should not be construed as an admission that any of the information it contains constitutes prior art against the present patent application.

SUMMARY

An embodiment that is described herein provides a method including holding in a memory of a receiver, for each temperature in a range of temperatures, a respective first parameter indicative of a frequency error of a crystal oscillator in the receiver at the temperature, and a respective second parameter indicative of an uncertainty of the first parameter. An operating temperature of the crystal oscillator is measured. One or more frequencies, for initial acquisition of signals from a transmitter, are selected based on the first and second parameters corresponding to the measured operating temperature. The receiver is tuned to receive the signals from the transmitter on at least one of the selected frequencies.

In some embodiments, holding the respective second parameter for each temperature includes holding a respective indication of a time that elapsed since updating of the corresponding first parameter. In an embodiment, selecting the frequencies includes calculating, based on the second parameter, a number of the frequencies to be selected, and selecting the calculated number of the frequencies.

In another embodiment, selecting the frequencies includes selecting a baseline frequency based on the first parameter, and selecting one or more additional frequencies at fixed frequency shifts from the baseline frequency. In yet another embodiment, tuning the receiver includes attempting to receive the signals on a given frequency among the selected frequencies, and progressing to receive the signals on another frequency among the selected frequencies upon a failure to receive the signals on the given frequency.

In a disclosed embodiment, the method includes defining, based on the second parameter, a respective time-out for receiving the signals on each of the selected frequencies, and tuning the receiver includes attempting to receive the signals on any of the selected frequencies for no more than the respective time-out. In an example embodiment, selecting the frequencies includes reducing the second parameter of the operating temperature based on the second parameter of another operating temperature, and choosing the frequencies for the operating temperature based on the reduced second parameter.

In some embodiments, holding the first and second parameters includes initializing the first and second parameters for each temperature based on characterization data measured for a type of the crystal oscillator. In an embodiment, holding the first and second parameters includes initializing the first and second parameters for each temperature by measuring two or more frequency errors of the crystal oscillator at two or more respective operating temperatures, and fitting a dependence of the frequency error on the operating temperature to the measured frequency errors.

In an embodiment, the method includes updating the first and second parameters corresponding to the measured operating temperature upon successfully communicating on one of the selected frequencies. In a disclosed embodiment, successfully communicating on the one of the selected frequencies includes successfully performing the initial acquisition on the one of the selected frequencies, and/or receiving the signals from the transmitter on the one of the selected frequencies above a predefined quality level. Additionally or alternatively, updating the first and second parameters includes filtering a current setting and one or more past settings of the first and second parameters.

There is additionally provided, in accordance with an embodiment that is described herein, apparatus including a receiver, a memory and control circuitry. The receiver is configured to receive signals. The memory is configured to hold for each temperature in a range of temperatures a respective first parameter indicative of a frequency error of a crystal oscillator in the receiver at the temperature, and a respective second parameter indicative of an uncertainty of the first parameter. The control circuitry is configured to obtain a measured operating temperature of the crystal oscillator, to select, based on the first and second parameters corresponding to the measured operating temperature, one or more frequencies for initial acquisition of the signals from a transmitter, and to tune the receiver to receive the signals from the transmitter on at least one of the selected frequencies.

In some embodiments, a mobile communication terminal includes the disclosed apparatus. In some embodiments, a chipset for processing signals in a mobile communication terminal includes the disclosed apparatus.

The present disclosure will be more fully understood from the following detailed description of the embodiments thereof, taken together with the drawings in which:

DETAILED DESCRIPTION OF EMBODIMENTS

Figure 1:
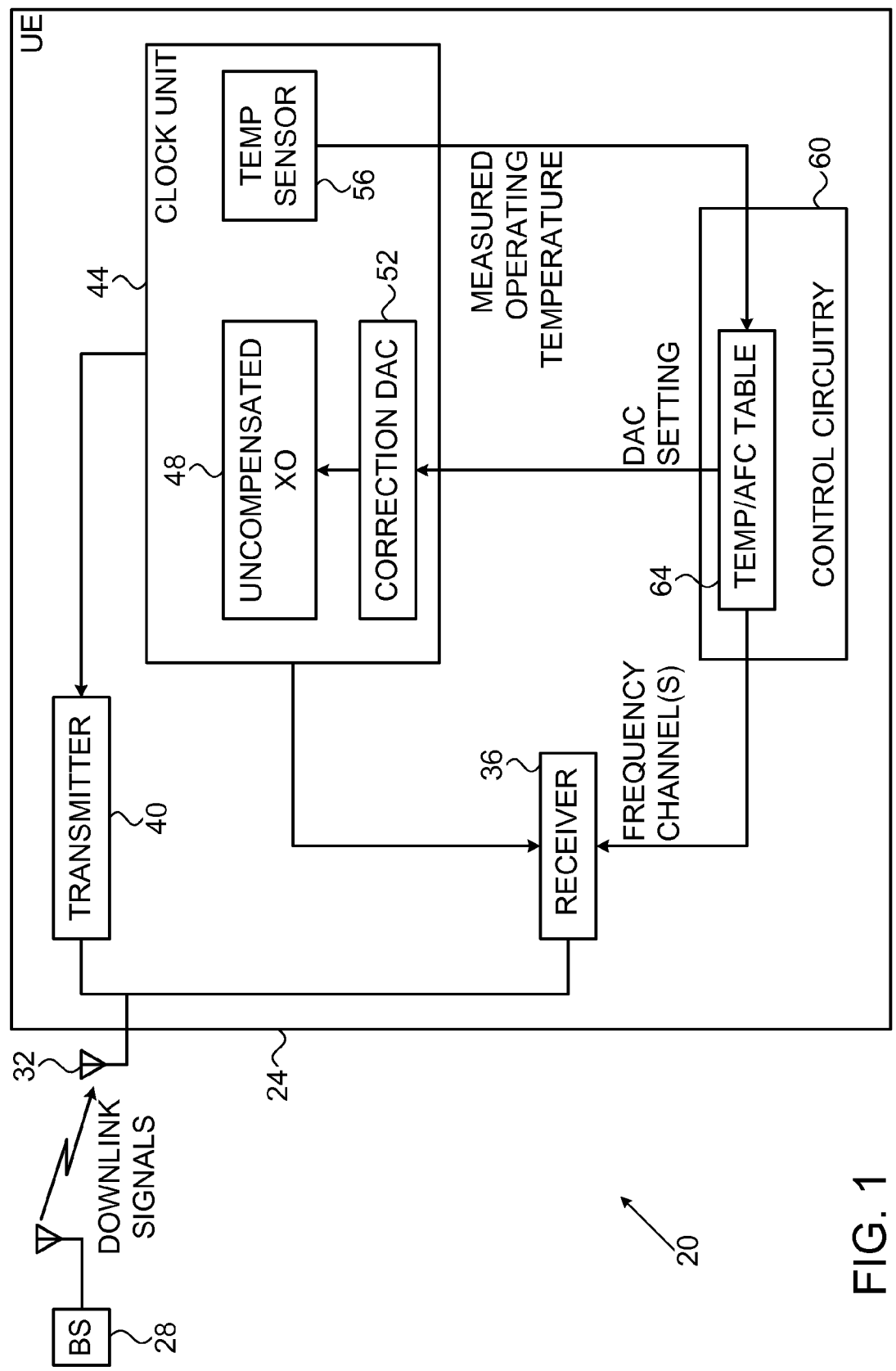
FIG. 1 is a block diagram that schematically illustrates a wireless communication system, in accordance with an embodiment that is described herein.

When a mobile communication terminal performs initial acquisition of a base station signal, one of the tasks of the terminal is to synchronize to the base station carrier frequency. Typically, the receiver in the terminal has a certain maximum frequency error that it is able to correct. If the frequency error between the terminal and the base station at the starting point of the acquisition process exceeds this maximum frequency error, the initial acquisition may fail.

When performing initial signal acquisition on a given frequency channel (e.g., Radio Frequency Channel Number—RFCN—in UMTS terminology), it is possible in principle for the terminal to correct large frequency errors by performing multiple acquisition attempts with different frequency shifts relative to the center frequency of the frequency channel. Such a process, however, increases the acquisition time considerably. The increase in acquisition time is particularly significant when the terminal searches for base station signals over a wide bandwidth, e.g., at power-up or following loss of service.

Embodiments that are described herein provide improved methods and apparatus for performing initial acquisition in mobile communication terminals. The disclosed techniques reduce the number of acquisition attempts per frequency channel. Therefore, these techniques facilitate the use of a low-cost uncompensated Crystal Oscillator (XO) as a clock source in the terminal, while at the same time maintaining acceptable acquisition time.

Although the embodiments described herein refer mainly to uncompensated XOs, the disclosed techniques are also applicable for improving the performance of terminals that use internally-compensated XOs, such as Temperature-Compensated XOs (TCXOs).

In some embodiments, the terminal is specified to operate over a certain temperature range. For each temperature in the range, the terminal holds a first parameter that is indicative of the frequency error of the terminal XO at the temperature, and a second parameter that is indicative of the uncertainty of the first parameter.

In an example embodiment, the first parameter comprises an Automatic Frequency Control (AFC) correction that is to be applied to the XO, and the second parameter comprises an indication of the time that elapsed since the AFC correction was last updated. The elapsed time is indicative of the uncertainty of the AFC correction, for example because the oscillator frequency drift over time.

When preparing to perform initial acquisition, control circuitry in the terminal measures the operating temperature of the XO and reads the first and second parameters corresponding to the measured operating temperature. Based on the read parameters, the control unit selects the number and frequency shifts of (one or more) acquisition attempts to be performed on each frequency channel. The control unit then configures the receiver to perform the initial acquisition accordingly.

In many practical scenarios, the uncertainty of the XO frequency error differs considerably from one temperature to another. For example, for some temperatures the frequency error may be known with relatively high accuracy, e.g., because the terminal has recently communicated successfully at these temperatures. For other temperatures the frequency error may have large uncertainty, e.g., when the frequency error was last measured during characterization of the type of crystal oscillator or during calibration of the terminal several years previously.

The mechanism described herein enables the control unit to match the number and frequencies of the initial acquisition attempts to the uncertainty of the XO frequency error at the specific operating temperature. When the uncertainty is small, the terminal receiver will typically perform a small number of acquisition attempts, or even a single attempt. When the uncertainty is large, the receiver will typically cover the uncertainty range using a larger number of acquisition attempts. In some embodiments, the control unit also sets a time-out for the acquisition attempts based on the second parameter, i.e., depending on the uncertainty of the XO frequency error.

When using this mechanism, the overall initial acquisition time of the terminal is reduced considerably. As a result, user experience is enhanced and battery time is extended. These performance improvements are important, for example, when the terminal uses an uncompensated crystal oscillator as a clock source.

FIG. 1 is a block diagram that schematically illustrates a wireless communication system 20, in accordance with an embodiment that is described herein. In the present example, system 20 comprises a cellular system that operates in accordance with the Universal Mobile Telecommunications System (UMTS) specifications. In alternative embodiments, system 20 may operate in accordance with any other suitable communication standard or protocol, such as, for example, Long Term Evolution (LTE), Digital Video Broadcasting (DVB), IEEE 802.16 (WiMAX) or Bluetooth.

In the example of FIG. 1, system 20 comprises a mobile communication terminal 24 (referred to in UMTS terminology as User Equipment—UE) that communicates with a base station 28 (referred to in UMTS terminology as NodeB). This choice is made, however, purely by way of example. In real-life configurations, system 20 typically comprises a large number of base stations and a large number of terminals. Terminal 24 may comprise, for example, a cellular phone, a wireless-enabled computing device or any other suitable type of communication terminal.

In the embodiment of FIG. 1, terminal 24 comprises at least one antenna 32 for receiving Radio Frequency (RF) downlink signals from base station 28 and for transmitting RF uplink signals to the base station. A receiver 36 receives the downlink signals via antenna 32, down-converts the signals and extracts downlink data from the signals. A transmitter 40 produces uplink signals, up-converts them to RF and transmits the RF uplink signals via antenna 32. Control circuitry 60 manages the operation of terminal 24. A clock unit 44 provides one or more clock signals to receiver 36 and transmitter 40. The clock signals are used, for example, for generating Local Oscillator (LO) signals for down-conversion and/or up-conversion, and for generating sampling clocks for analog-to-digital and/or digital-to-analog conversion in the receiver and transmitter.

Figure 2:
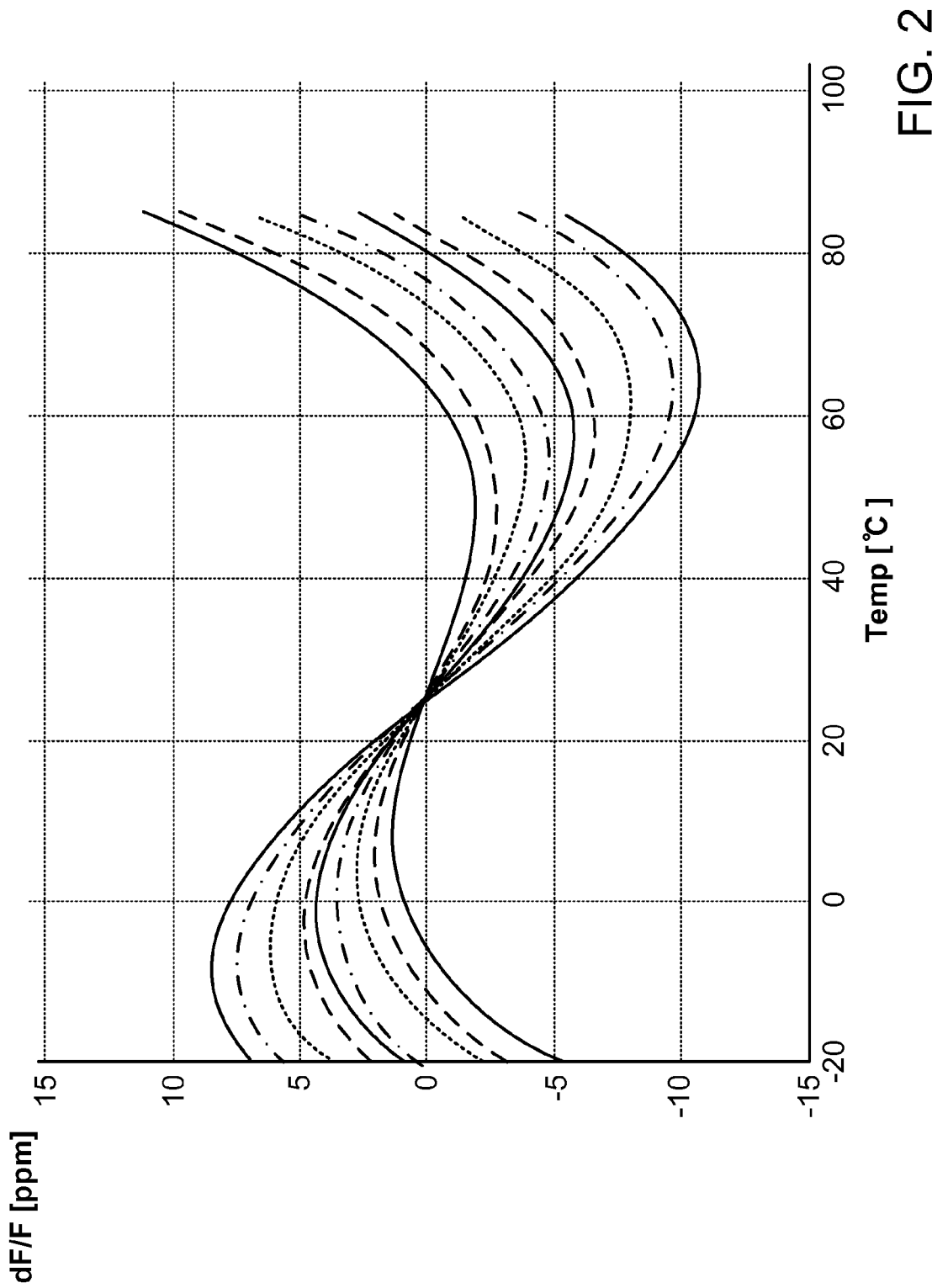
FIG. 2 is a graph showing frequency error as a function of temperature for multiple uncompensated Crystal oscillators.

In the present example, clock unit 44 comprises an uncompensated crystal oscillator (XO) 48 that is used as a clock reference for the (one or more) clock signals produced by the clock unit. In the present context, the term "uncompensated" means that XO 48' has no internal circuitry for correcting frequency errors due to temperature variations, such as mechanisms used in TCXOs and Voltage-Controlled TXCOs (VCTCXOs). In an embodiment, XO 48 comprises an AT-cut XO such as the model NX3225DA XO, available from Nihon Dempa Kogyo Co., Ltd (NDK) of Japan, whose frequency accuracy is specified as ±11 ppm over −20° C. to +80° C. Example plots of frequency error over temperature for this type of crystal oscillator are shown in FIG. 2 below. In alternative embodiments, XO 48 may comprise any other suitable XO.

In an embodiment, clock unit 44 comprises a correction Digital to Analog Converter (DAC) 52. DAC 52 is controlled by control circuitry 60, and produces an analog voltage or current that adjusts the frequency of XO 48. In the example of FIG. 1 DAC 52 is part of clock unit 44. In an alternative embodiment DAC 52 is part of control circuitry 60. By writing suitable digital correction values to DAC 52, the control circuitry is able to apply corrections to the frequency of XO 48. The correction values written by control circuitry 60 to DAC 52 are also referred to herein as Automatic Frequency Control (AFC) values.

In an embodiment, clock unit 44 further comprises a temperature sensor 56. The output of temperature sensor 56 is used as an estimate of the operating temperature of XO 48, and therefore the temperature sensor is typically mounted in close proximity to the XO, for example, adjacently to the XO on the same Printed Circuit Board (PCB). The output of sensor 56 is read by control circuitry 60.

In some embodiments, control circuitry 60 comprises a temperature/AFC table 64, which holds correction values for correcting the frequency of XO 48. Table 64 holds multiple AFC values for DAC 52 corresponding to respective operating temperatures. In addition, for each temperature, table 64 holds at least one uncertainty parameter that is indicative of the uncertainty of the AFC value at that temperature. In some embodiments the uncertainty parameter of each temperature comprises a combination of two or more parameters held in table 64. Control circuitry 60 uses the information in table 64 to perform fast and efficient initial acquisition of the signals of base station 28, as will be explained in detail below. Table 64 is typically stored in a suitable memory device in terminal 24.

The terminal configuration shown in FIG. 1 is an example configuration, which is depicted in a highly simplified manner solely for the sake of clarity. In alternative embodiments, any other suitable terminal configuration can be used. Terminal elements that are not mandatory for understanding of the disclosed techniques have been omitted from the figure for the sake of clarity. Further aspects of operating communication terminals using uncompensated crystal oscillators are addressed, for example, in U.S. Pat. No. 8,031,024, whose disclosure is incorporated herein by reference.

In various embodiments, some or all of the elements of terminal 24, including receiver 36, transmitter 40, clock unit 44 and control circuitry 60, are implemented in hardware, such as implementing elements of the transmitter and receiver using one or more Radio Frequency Integrated Circuits (RFICs), or implementing the elements of the transmitter, the receiver and/or the control circuitry using one or more Field-Programmable Gate Arrays (FPGAs) or Application-Specific Integrated Circuits (ASICs). In alternative embodiments, certain elements of terminal 24 are implemented in software, or using a combination of hardware and software elements.

In some embodiments, certain terminal elements, such as certain elements of control circuitry 52, are implemented in a programmable processor, which is programmed in software to carry out the functions described herein. The software may be downloaded to the processor, in whole or in part, in electronic form, over a network, for example, or it may, alternatively or additionally, be provided and/or stored on non-transitory tangible media, such as magnetic, optical, or electronic memory.

FIG. 2 is a graph showing the frequency error dF/F as a function of temperature for a batch of uncompensated NDK NX3225DA XOs. Each plot in the figure illustrates the frequency error of a respective individual XO of this type over a range of temperatures. As can be seen in the figure, the frequency error follows the same general behavior, but may differ from one XO to another.

The frequency accuracy of this type of XO is specified at ±11 ppm over −20° C. to 80° C. The frequency error is assumed to be calibrated at 25° C., and therefore the multiple plots intersect at that temperature for which dF/F=0. The calibration range at this temperature is typically in the order of 10 ppm, for example due to soldering, parasitic capacitances, voltage tolerance and other factors. In addition, aging effects typically contribute an error on the order of 1 ppm/year. The aging rate typically reduces over time in a logarithmic dependence. In addition, thermal hysteresis typically occurs when the XO is heated and then cooled. The error when returning to the same temperature is on the order of 0.5 ppm. The figure also shows that the slope of the frequency variation with temperature is bounded by 0.6 ppm/° C.

The frequency variation as a function of temperature for this sort of AT-cut XO can be modeled by a third-order polynomial of the form:

$$\frac{\Delta f(t)}{f} = A(T - T_0) + B(T - T_0)^2 + C(T - T_0)^3 \qquad \text{Equation 1}$$

wherein $T_0=26°$ C. Each individual plot in FIG. 2, i.e., each frequency-temperature dependence of an individual XO, corresponds to a respective selection of crystal coefficients A, B and C.

(As can be seen in FIG. 2, although the XO is uncompensated, it does not necessarily mean that at any given temperature it will have a larger range of possible frequencies compared to a compensated XO. The uncompensated XO typically has a generally consistent finite frequency error as a function of frequency, which may also drift over time. In other words, at a given temperature, subject to drift, the uncompensated XO will consistently achieve a similar frequency. Ultimately, however, the certainty that the actual frequency achieved by the uncompensated XO is a desired frequency is low.)

When terminal 24 performs initial acquisition of the signals of base station 28, receiver 36 attempts to lock on a common channel that is transmitted by the base station. In UMTS, for example, the base station transmits a Synchronization Channel (SCH) and a Common Pilot Channel (CPICH). The terminal typically attempts to lock on the SCH first, in order to obtain the base station timing. Then, the terminal attempts to lock on the CPICH to obtain the base station scrambling code. Once the timing and scrambling code are available, the terminal is able to start exchanging data with the base station. Further details regarding initial acquisition in UMTS are provided, for example, in 3GPP TS 25.214, Annex C, and in 3GPP TS 25.211, chapter 5, cited above.

During the initial acquisition process, terminal 24 also locks on the carrier frequency of the base station downlink signal. In accordance with the UMTS specifications cited above, the terminal is allowed to transmit uplink signals to the base station only when the frequency error between the terminal and the base station is less than ±0.1 ppm. In the 2 GHz frequency band, this frequency error translates to ±200 Hz. This frequency error is considerably smaller than the uncompensated frequency error of XO 48, which in the present example is on the order of ±11 ppm corresponding to ±22 KHz at 2 GHz. (The examples given herein refer to operation in the 2 GHz band. The disclosed techniques and considerations, however, are similarly applicable to any other frequency band.)

Typically, receiver 36 of terminal 24 locks onto the base station carrier frequency over the CPICH signal, e.g., because the CPICH has a better Signal to Noise Ratio (SNR) than the SCH and is transmitted continuously. The CPICH has a symbol rate of 15 KHz, meaning that receiver 36 can use the CPICH to detect and correct frequency errors of up to ±7.5 KHz ideally. In practice, the allowed range of frequency error correctable by the receiver is limited to approximately ±6 KHz.

As noted above, XO 48 has an uncompensated frequency error of up to ±22 KHz, which is considerably larger than the allowed frequency error range of receiver 36. Thus, unless the XO frequency is corrected, receiver 36 may not be able to perform initial acquisition reliably using XO 48 as a clock source.

It is possible in principle to overcome the above problem by performing multiple acquisition attempts in receiver 36, using shifted carrier frequencies. The frequency shifts can be applied by setting DAC 52 to different AFC values, and attempting to perform acquisition for each AFC value. The gap between the ±6 KHz allowed range of the receiver and the ±22 KHz range of the XO can be overcome, for example, by performing four acquisition attempts using receiver frequency shifts of ±5.5 KHz and ±16.5 KHz relative to the receiver's center frequency. Each acquisition attempt using a certain frequency shift is referred to as a hypothesis.

This solution, however, significantly increases the acquisition time of terminal 24, and the resulting acquisition time may be intolerable in some cases. For example, when terminal 24 performs a full scan of multiple RF bands in search of a base station (e.g., at power on or in out-of-service conditions), receiver 36 would scan a large number of RF Channel Numbers (RFCNs). Since most RFCNs typically do not carry a valid downlink signal, receiver 36 would spend considerable time performing futile acquisition attempts. If the receiver needs to attempt four hypotheses (±5.5 KHz, ±16.5 KHz) for each RFCN, the acquisition time would be quadrupled. As a result, user experience is degraded and battery time of terminal 24 is reduced.

In some embodiments, control circuitry 60 in terminal 24 uses the information in temperature/AFC table 64 to reduce the number of hypotheses that are performed by receiver 36 during initial acquisition. In an embodiment, table 64 holds, for each temperature within a range of operating temperatures of XO 48, a respective AFC value (a frequency correction) for correcting the frequency error of XO 48 at that temperature. In addition, table 64 holds for each temperature a respective uncertainty parameter, which is indicative of the uncertainty of the AFC value of that temperature.

For a given temperature, control circuitry 60 in this example uses the uncertainty parameter to determine the number of hypotheses (frequency shifts) to be performed around the AFC value (i.e., around the baseline frequency at the center of the channel in question).

The uncertainty parameter may vary from one temperature to another. Consider, for example, a temperature for which the AFC value in table 64 was set during a characterization process several years previously. This AFC value would typically be assigned high uncertainty, and therefore receiver 36 would typically attempt multiple hypotheses around it. At the other extreme, consider a temperature for which the AFC value in table 64 was updated several days ago, when receiver 36 successfully communicated at that temperature. Such an AFC value would typically be assigned low uncertainty. Receiver 36 would typically attempt only a small number of hypotheses around this AFC value, possibly only a single hypothesis.

In an example embodiment, temperature/AFC table 64 is of the following form:

TABLE 1

Example temperature/AFC table

| Temperature [° C.] | AFC value | Date of last AFC value update | Uncertainty excluding aging [ppm] |
|---|---|---|---|
| −20 | 2100 | Characterization (Jan. 1, 2009) | ±5.5 |
| −19 | 2120 | Characterization (Jan. 1, 2009) | ±5.5 |
| ... | ... | ... | ... |
| 25 | 2000 | Feb. 1, 2012 | ±0.5 |
| ... | ... | ... | ... |
| 79 | 2330 | Jan. 1, 2009 | ±0.5 |
| 80 | 2350 | Jan. 1, 2009 | ±0.5 |

In the example of Table 1, the first column gives the operating temperature of XO 48, the second column gives the central AFC value for that temperature, the third column gives the date in which the AFC value of that temperature was last updated, and the fourth column gives an uncertainty in the AFC value of that temperature other than aging. In this example, the parameters in the third and fourth columns are jointly regarded as the uncertainty parameter.

In the present example, the range of AFC values (the range of digital values written to DAC 52) is 0 . . . 4000, and this range covers a frequency correction range of ±15 ppm. Thus, the resolution of the frequency correction using DAC 52 is 60 KHz/4000=15 Hz in the 2 GHz band, and 27 KHz/4000=6.75 Hz in the 900 MHz band. In alternative embodiments, any other suitable AFC value range and resolution can be used.

In an embodiment, when terminal 24 prepares to perform initial acquisition on a certain RFCN, control circuitry 60 reads temperature sensor 56 to obtain the current operating temperature of XO 48. The control circuitry then reads the table entry (row) of table 64 corresponding to the measured temperature, and calculates a frequency error denoted InitialError based on the uncertainty parameter in the table entry.

If the table entry holds a calibration value, the control circuitry calculates InitialError=TempDependentCalibError+AgingRate×(Rtc−StoredDate/1 Year), wherein TempDependentCalibError denotes the uncertainty excluding aging (read from the fourth column of table 64), AgingRate denotes the aging-related drift of XO 48 in ppm/year (in the present example 1 ppm/year), Rtc denotes the current time, and StoredDate denotes the date in which the AFC value was last updated (read from the third column of table 64).

If the table entry does not hold a calibration value, the control circuitry calculates InitialError=0.5+AgingRate×(Rtc−StoredDate/1Year), wherein the 0.5 ppm value estimates the total uncertainty other than aging, for example due to temperature measurement errors, thermal hysteresis or any other source of impairment.

In this embodiment, control circuitry 60 sets the initial XO frequency (initial hypothesis), denoted InitialAfcDac, in accordance with the AFC value of the measured operating temperature (read from the second column of table 64). The control circuitry selects the number of hypotheses around InitialAfcDac based on the uncertainty InitialError.

Assume, for example, that control circuitry 60 reads a temperature of 25° C. from sensor 56, and accesses the corresponding row in table 64. Since this entry (in the example of Table 1 above) was updated recently, it has a small aging-related uncertainty. As explained above, the ±0.5 ppm uncertainty represents the total uncertainty due to temperature measurement errors, thermal hysteresis or other impairment source. In this example, the uncertainty of the AFC value is small enough such that receiver 36 is able to perform only a single hypothesis, i.e., perform a single acquisition attempt using the AFC value 2000 given in Table 1.

As another example, assume that control circuitry 60 reads a temperature of 80° C. from sensor 56, and accesses the corresponding row in table 64. In the example, this entry in the table was updated three years ago (assuming e.g. the present time is January 2012), aging-related drift can add up to ±3 ppm to the uncertainty of the AFC value. The overall uncertainty is thus ±3.5 ppm. For operation in the 2 GHz band, the ±3.5 ppm uncertainty translates to ±7 KHz, which is beyond the ±6 KHz that receiver 36 is able to handle in a single acquisition attempt (hypothesis).

In this case, control circuitry 60 instructs receiver 36 to perform two acquisition attempts with AFC values of ±200 around the 2350 AFC value read from table 64, i.e., AFC values 2350+200 and 2350−200. (The 200 AFC value offset is derived from a desired offset of 3 KHz divided by the 15 Hz resolution of DAC 52.) By performing these two acquisition attempts, receiver 36 covers the entire ±7 KHz uncertainty range.

For operation in the 900 MHz band, the same uncertainty at 80° C. translates to only ±3.15 kHz, which can be covered by a single hypothesis. Receiver 36 thus performs a single acquisition attempt with the AFC value of 2350 read from table 64. As can be seen in the above example, at 80° C. terminal 24 will exhibit an increased acquisition time only in the 2 GHz band, while acquisition time in the 900 MHz remains relatively short.

As yet another example, assume that control circuitry 60 reads a temperature of −20° C. from sensor 56, and accesses the corresponding row in table 64. The table entry for −20° C. (in the example of Table 1) was set only during characterization, three years ago. Assuming that the characterization process has an error of ±5.5 ppm (as will be explained later) and aging over three years adds up to ±3 ppm to this error, the overall uncertainty becomes ±8.5 ppm.

For operation in the 2 GHz band, the ±8.5 ppm uncertainty translates to an uncertainty of ±17 kHz, which is larger than the ±6 KHz that receiver 36 can cover in a single acquisition attempt. In this case, control circuitry 60 instructs receiver 36 to perform three acquisition attempts around the AFC value 2100 read from table 64. The three acquisition attempts are performed at AFC values of 2100-800, 2100 and 2100+800. The 800 value is derived from a desired 12 KHz frequency offset, divided by the 15 Hz resolution of DAC 52. The three hypotheses cover the entire ±17 kHz uncertainty range.

For operation in the 900 MHz band, the ±8.5 ppm uncertainty at −20° C. translates to only ±7.65 kHz that can be covered in two hypotheses. Control circuitry 60 therefore instructs the receiver to perform two acquisition attempts, with AFC DAC values of 2100+444 and 2100444. The 444 value is derived from a desired 3 KHz frequency offset, divided by the 6.75 Hz resolution of DAC 52. The two hypotheses cover the entire ±17 kHz uncertainty range.

The examples above demonstrate that, when using the disclosed techniques, the acquisition time grows with the frequency correction uncertainty, but it is maintained at the optimal value.

In some embodiments, control circuitry 60 reduces the uncertainty parameter for a given temperature using an uncertainty parameter of a nearby temperature. This improvement uses the fact that the frequency variation of XO 48 as a function of temperature is typically bounded by some maximum slope. In the present example, the maximum possible slope (the steepest slope in the plots of FIG. 2 over the relevant temperature range) is 0.6 ppm/° C. Using this bound, control circuitry 60 can in some cases obtain a reduced uncertainty parameter for a certain temperature, and thus reduce the number of acquisition attempts at that temperature.

In an example embodiment, in addition to the uncertainty InitialError defined above, control unit 60 calculates for a given temperature an uncertainty InitialError2=0.5÷AgingRate×(Rtc-StoredDate/1Year)+MaxSlope×ΔT, wherein MaxSlope denotes the maximum XO frequency variation with temperature (0.6 ppm/° C. in the present example), and ΔT denotes the temperature difference (in ° C.) between the given temperature and a nearby temperature for which the uncertainty is small (e.g., for which the AFC value was updated recently). (In this embodiment, the StoredDate value should also be taken from the nearby temperature entry, and not from the requested temperature.)

If InitialError2 is smaller than InitialError, then the control circuitry substitutes InitialError2 for InitialError and uses the smaller uncertainty for determining the number of acquisition attempts for the given temperature. The same is true for the AFC DAC entry that is taken from the nearby temperature entry.

For example, assume that the temperature/AFC table of Table 1 above further contains the following entry for −15° C.:

| Temperature [° C.] | AFC value | Date of last AFC value update | Uncertainty excluding aging [ppm] |
|---|---|---|---|
| −15 | 2150 | Jan. 1, 2012 | ±0.5 |

In an embodiment, when preparing to perform initial acquisition at −20° C., control circuitry 60 calculates a reduced uncertainty for −20° C. using the entry for −15° C. Since the frequency variation slope of XO 48 is bounded by 0.6 ppm/° C., the uncertainty of the AFC value for −20° C. can be reduced to ±(0.5+5° C.×0.6 ppm/° C.)=±3.5 ppm. This uncertainty is considerably smaller than the ±8.5 ppm calculated in the previous example (i.e., without considering nearby temperatures). In some embodiments, the aging of each entry is also considered in the comparison, and may change the selection decision.

In various embodiments, control circuitry 60 uses different nearby temperatures for reducing the uncertainty at a given temperature. For example, the control circuitry may use the next-higher temperature that holds a small uncertainty parameter and/or the next-lower temperature that holds a small uncertainty parameter. In an embodiment, control circuitry 60 conducts this process for temperatures that hold calibration uncertainties and/or for temperatures in which the last update of the AFC value was performed more than a predefined time ago (e.g., three months or more).

In some embodiments, in addition to selecting the number of acquisition attempts for a given temperature, control circuitry 60 sets a time-out that gives the maximum duration of each acquisition attempt. In other words, the time-out assigned to an acquisition attempt is the maximum time duration that receiver 36 spends on the respective frequency offset before declaring failure and moving to the next acquisition attempt. In an example embodiment, control circuitry 60 instructs receiver 36 to perform hypotheses and apply time-out values according to the following table, in which the time-out per hypothesis is given as a function of the uncertainty parameter InitialError:

TABLE 2

Hypotheses and time-outs per uncertainty

| Initial Error [KHz] | Number of acquisition attempts (hypotheses) | Frequency shifts of hypotheses [Khz] | Time-out per hypothesis [seconds] |
|---|---|---|---|
| \|dF\| < 3 | 1 | 0 | 0.5 |
| 3 < \|dF\| < 4 | 1 | 0 | 1.5 |
| 4 < \|dF\| < 5 | 1 | 0 | 2.0 |
| 5 < \|dF\| < 6 | 1 | 0 | 2.5 |
| 6 < \|dF\| < 10 | 2 | ±5 | 2.5 |
| 10 < \|dF\| < 14 | 3 | 0, ±10 | 2.5 |
| 14 < \|dF\| < 18 | 4 | ±5, ±15 | 2.5 |
| 18 < \|dF\| < 22 | 5 | 0, ±10, ±20 | 2.5 |

In alternative embodiments, control circuitry 60 may set the time-out per hypothesis in any other suitable manner.

Figure 3:
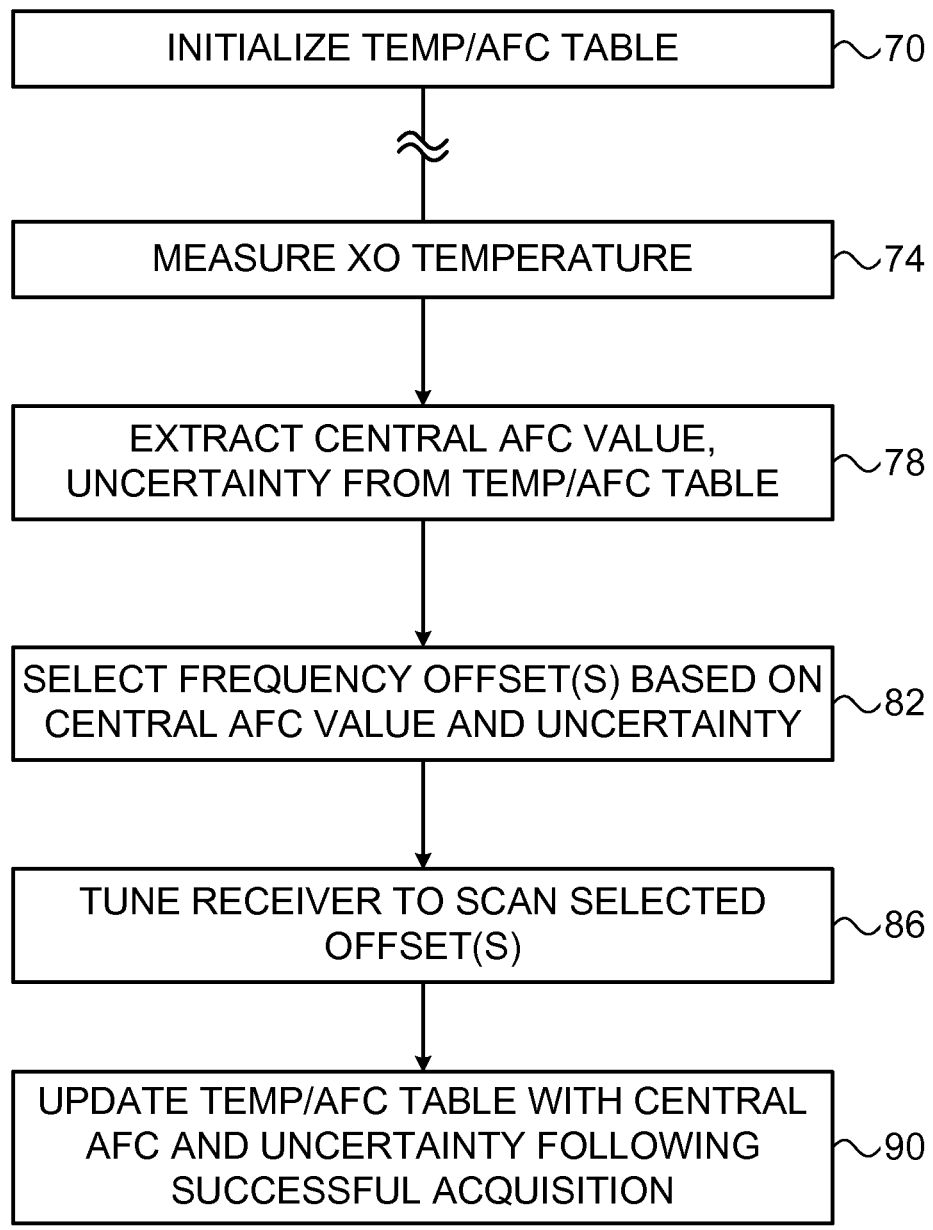
FIG. 3 is a flow chart that schematically illustrates a method for initial acquisition in a mobile communication terminal, in accordance with an embodiment that is described herein.

FIG. 3 is a flow chart that schematically illustrates a method for initial acquisition in a mobile communication terminal, in accordance with an embodiment that is described herein. The method begins with control circuitry 60 in terminal 24 initializing temperature/AFC table 64 with AFC values and uncertainty parameters per temperature, at an initialization operation 70. Several example techniques for initializing table 64 are described further below.

When preparing to perform initial acquisition of a base station, control circuitry 60 reads the current XO operating temperature from sensor 56, at a temperature measurement operation 74. Control circuitry 60 extracts from table 64 the AFC value and uncertainty parameter that are applicable to the measured temperature, at a table querying operation 78.

The control circuitry then selects the (one or more) frequencies to be used for acquisition attempts per RFCN, at a frequency selection operation 82. In some embodiments, control circuitry 60 selects the number of acquisition attempts and their relative frequency offsets based on the uncertainty parameter, for example using a table such as Table 2 above. In some embodiments, the control circuitry also selects the time-out to be used in each acquisition attempt, for example using a table such as Table 2 above.

Control circuitry 60 tunes receiver 36 to the selected frequencies, at a tuning operation 86. Receiver 36 attempts to acquire the base station signal on these frequencies. Upon successful acquisition, control circuitry 60 updates the applicable entry in table 64 with an updated AFC value, and resets the uncertainty parameter, at a table updating operation 90.

In some embodiments, control circuitry 60 also updates the table during normal operation of the receiver, for example when the receiver verifies that reception conditions are sufficiently good (e.g., above some predefined quality level). This mechanism enables a more frequent update of the table, which typically also leads to updating the table over a wider range of temperatures (as opposed to updating the table only upon the relatively rare occasion of performing initial acquisition).

In some embodiments, control circuitry 60 initializes table 64 with initial AFC values and uncertainty parameters using the known characteristic of the type of XO, e.g., by fitting the data of FIG. 2 above. In an example embodiment, the AFC value of each temperature is initialized to the median value of the plots of FIG. 2 data points for that temperature. The uncertainty parameter of each temperature is initialized to the maximum deviation from the median for that temperature in the plots of FIG. 2.

This initial uncertainty parameter using this technique is considerably less than 11 ppm. As can be seen in FIG. 2, for the temperature range 5° C.-45° C. the initial uncertainty is less than 3 ppm. This initial uncertainty means that initial acquisition can be performed using a single hypothesis per RFCN, even in the 2 GHz band, as long as aging is small. For temperatures outside the 5° C.-45° C. range, two or more hypotheses typically are needed per RFCN to cover the initial uncertainty. In the extreme case of 80° C., the uncertainty is ±7.5 ppm relative to the median value. In this case, even in the 2 GHz band, three hypotheses with frequency shifts of 0 and ±5 ppm are sufficient to ensure successful acquisition.

In some embodiments, control circuitry 60 initializes the AFC values in table 64 based on a calibration- process that estimates the crystal coefficients A, B and C and $T_0$ (defined in Equation 1 above) for the specific XO of terminal 24. In such a calibration process, circuitry 60 typically measures the actual frequency error of XO 48 for multiple temperatures, and the XO operating temperature corresponding to each frequency error measurement. Four or more such measurements are sufficient for deriving A, B and C and $T_0$. Once $T_0$ and the three crystal coefficients are known, $$\frac{\Delta f(t)}{f}$$

of Equation 1 can be evaluated for any temperature, and the AFC values of table 64 are initialized with the values of $$\frac{\Delta f(t)}{f}.$$

In some embodiments, the initialization process above can be simplified by setting certain average values for B, C and $T_0$, performing a small number (two or more) of frequency-temperature measurements, and estimating only A. The simplified process is less accurate than full estimation of A, B and C and $T_0$, but nevertheless reduces the initial uncertainty. For example, simulation has shown that using two calibration points at 30° C. and 40° C. and using realistic assumptions regarding impairments, the calibration process is able to reduce the initial uncertainty to ±4 ppm. This initial uncertainty can be covered in two hypotheses, instead of three hypotheses when relying on characterization data.

As noted above, when receiver 36 succeeds in locking on the signal of base station 28, control circuitry 60 updates the entry of table 64 that corresponds to the current operating temperature. Typically, following successful acquisition the frequency error of XO 48 is less than 0.2 ppm. Thus, control circuitry 60 updates the AFC value of the current operating temperature in table 64 with the AFC value that yielded successful acquisition, and resets the corresponding uncertainty parameter (e.g., enters the time at which acquisition succeeded). This sort of updating also reduces the uncertainty caused by aging drift.

In some embodiments, control circuitry 60 updates table 64 whenever the current AFC value is considered valid. Control circuitry 60 may consider the AFC value valid based on any suitable criterion, for example when the downlink signal SNR is above a certain threshold, when the downlink signal Bit Error Rate (BER) or Block Error Rate (BLER) is below a certain threshold, or based on any other suitable quality metric of the downlink signal.

In some embodiments, control unit 60 applies certain filtering to the previous and new AFC values before updating. In an example embodiment, the control circuitry calculates a weighted combination of the existing AFC value in table 64 and the updated AFC value, and stores the weighted combination as the updated AFC value in the table. Filtering of this sort helps to mitigate impairments such as Doppler-related errors and thermal hysteresis.

It is noted that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
   holding in a memory of a receiver, for multiple temperatures, (i) respective first parameters indicative of frequency errors of a crystal oscillator in the receiver at the respective temperatures, and (ii) respective second parameters that specify whether the corresponding first parameters were most-recently updated during successful operation of the receiver at the respective temperatures or only during initial characterization of the crystal oscillator;
   measuring an operating temperature of the crystal oscillator;
   selecting a center frequency based on one of the first parameters corresponding to the measured operating temperature;
   selecting, based on one of the second parameters corresponding to the measured operating temperature, a size of a frequency uncertainty range around the center frequency, over which to attempt initial acquisition of signals from a transmitter; and
   tuning the receiver to acquire the signals from the transmitter over the selected frequency uncertainty range around the center frequency.

2. The method according to claim 1, wherein selecting the size of the frequency uncertainty range comprises calculating, based on the selected one of the second parameters, a number of frequencies in the selected frequency uncertainty range over which to attempt the initial acquisition, and selecting the calculated number of the frequencies.

3. The method according to claim 1, wherein tuning the receiver comprises attempting to receive the signals on a given frequency among selected frequencies in the selected frequency uncertainty range, and progressing to receive the signals on another frequency in the selected frequency uncertainty range upon a failure to receive the signals on the given frequency.

4. The method according to claim 1, comprising defining, based on the selected one of the second parameters, a respective time-out for receiving the signals on each of selected frequencies in the selected frequency uncertainty range, wherein tuning the receiver comprises attempting to receive the signals on any of the selected frequencies for no more than the respective time-out.

5. The method according to claim 1, wherein selecting the size of the frequency uncertainty range comprises reducing a value of the selected one of the second parameters of the operating temperature based on a second parameter of another operating temperature, and choosing the size of the frequency uncertainty range for the operating temperature based on the reduced value of the selected one of the second parameters.

6. The method according to claim 1, wherein holding the respective first and second parameters comprises initializing the respective first and second parameters based on characterization data measured for a type of the crystal oscillator.

7. The method according to claim 1, wherein holding the respective first and second parameters comprises initializing the respective first and second parameters by measuring two or more frequency errors of the crystal oscillator at two or more respective operating temperatures, and fitting a dependence of the frequency error on the operating temperature to the measured frequency errors.

8. The method according to claim 1, comprising updating the respective first and second parameters corresponding to the measured operating temperature upon successfully communicating on one of selected frequencies in the selected frequency uncertainty range.

9. The method according to claim 8, wherein successfully communicating on the one of the selected frequencies comprises at least one of:
   successfully performing the initial acquisition on the one of the selected frequencies; and
   receiving the signals from the transmitter on the one of the selected frequencies above a predefined quality level.

10. The method according to claim 8, wherein updating the respective first and second parameters comprises filtering a current setting and one or more past settings of the respective first and second parameters.

11. Apparatus, comprising:
   a receiver, which is configured to receive signals;
   a memory, which is configured to hold, for multiple temperatures, (i) respective first parameters indicative of frequency errors of a crystal oscillator in the receiver at the respective temperatures, and (ii) respective second parameters that specify whether the corresponding first parameters were most-recently updated during successful operation of the receiver at the respective temperatures or only during initial characterization of the crystal oscillator; and
   control circuitry, which is configured to obtain a measured operating temperature of the crystal oscillator, to select a center frequency based on one of the first parameters corresponding to the measured operating temperature, to select, based on one of the second parameters corresponding to the measured operating temperature, a size of a frequency uncertainty range around the center frequency, over which to attempt initial acquisition of the signals from a transmitter, and to tune the receiver to acquire the signals from the transmitter over the selected frequency uncertainty range around the center frequency.

12. The apparatus according to claim 11, wherein the control circuitry is configured to calculate, based on the selected one of the second parameters, a number of frequencies in the selected frequency uncertainty range over which to attempt the initial acquisition, and to select the calculated number of the frequencies.

13. The apparatus according to claim 11, wherein the control circuitry is configured to define, based on the selected one of the second parameters, a respective time-out for receiving the signals on each of selected frequencies in the selected frequency uncertainty range, and to tune the receiver to receive the signals on any of the selected frequencies for no more than the respective time-out.

14. The apparatus according to claim 11, wherein the control circuitry is configured to reduce a value of the selected one of the second parameters of the operating temperature based on a second parameter of another operating temperature, and to choose the size of the frequency uncertainty range for the operating temperature based on the reduced value of the selected one of the second parameters.

15. The apparatus according to claim 11, wherein the control circuitry is configured to initialize the respective first and second parameters by performing one of:

initializing the respective first and second parameters based on characterization data measured for a type of the crystal oscillator; and initializing the respective first and second parameters by measuring two or more frequency errors of the crystal oscillator at two or more respective operating temperatures, and fitting a dependence of the frequency error on the operating temperature to the measured frequency errors.

16. The apparatus according to claim 11, wherein the control circuitry is configured to update the respective first and second parameters corresponding to the measured operating temperature upon successfully communicating on one of selected frequencies in the selected frequency uncertainty range.

17. The apparatus according to claim 16, wherein the control circuitry is configured to update the respective first and second parameters upon carrying out at least one of:

successfully performing the initial acquisition on the one of the selected frequencies; and receiving the signals from the transmitter on the one of the selected frequencies above a predefined quality level.

18. The apparatus according to claim 16, wherein the control circuitry is configured to filter a current setting and one or more past settings of the respective first and second parameters before updating the respective first and second parameters.

19. A mobile communication terminal comprising the apparatus of claim 11.

20. A chipset for processing signals in a mobile communication terminal, comprising the apparatus of claim 11.

* * * * *